United States Patent
Kim (10) Patent No.: US 9,872,743 B2
(45) Date of Patent: Jan. 23, 2018

(54) CLEAR ALIGNER SET AND ORTHODONTIC TREATMENT METHOD CONSIDERING RESILIENCE OF HUMAN BODY

(71) Applicant: eClear International Co., Ltd., Los Angeles, CA (US)

(72) Inventor: Taeweon Kim, Seoul (KR)

(73) Assignee: eClear International Co., Ltd., Los Angeles, CA (US)

( * ) Notice: Subject to any disclaimer, the term of this patent is extended or adjusted under 35 U.S.C. 154(b) by 0 days.

(21) Appl. No.: 15/051,881

(22) Filed: Feb. 24, 2016

(65) Prior Publication Data

US 2017/0239018 A1    Aug. 24, 2017

(51) Int. Cl.
| | |
|---|---|
| *A61C 7/08* | (2006.01) |
| *B33Y 80/00* | (2015.01) |
| *B29C 51/10* | (2006.01) |
| *B29L 31/00* | (2006.01) |

(52) U.S. Cl.
CPC ............. *A61C 7/08* (2013.01); *B29C 51/10* (2013.01); *B33Y 80/00* (2014.12); *B29K 2995/0026* (2013.01); *B29L 2031/753* (2013.01)

(58) Field of Classification Search
CPC .. A61C 7/08; A61C 7/00; B33Y 80/00; B29K 2995/0026; B29L 2031/753
USPC ...................................................... 433/6, 24
See application file for complete search history.

(56) References Cited

U.S. PATENT DOCUMENTS

| | | | | |
|---|---|---|---|---|
| 5,975,893 A | * | 11/1999 | Chishti | A61C 7/00 433/24 |
| 7,059,850 B1 | * | 6/2006 | Phan | A61C 7/00 433/24 |
| 2003/0190575 A1 | * | 10/2003 | Hilliard | A61C 7/00 433/6 |
| 2006/0008760 A1 | * | 1/2006 | Phan | A61C 7/00 433/6 |
| 2010/0129763 A1 | * | 5/2010 | Kuo | A61C 7/08 433/6 |
| 2011/0247214 A1 | * | 10/2011 | Huge | A61C 7/002 29/896.11 |
| 2012/0150494 A1 | * | 6/2012 | Anderson | A61C 7/002 703/1 |
| 2013/0122447 A1 | * | 5/2013 | Lemchen | A61C 7/08 433/24 |
| 2013/0122448 A1 | * | 5/2013 | Kitching | A61C 7/002 433/24 |

(Continued)

*Primary Examiner* — Nicholas Lucchesi
(74) *Attorney, Agent, or Firm* — Stuart H. Mayer; Mayer & Williams PC (57) ABSTRACT

Provided are a clear aligner set and an orthodontic treatment method considering resilience of a human body. The clear aligner set may include at least one first clear aligner, having a first restoring force to apply a first pressing force to teeth during a first period, and primarily wearable by an orthodontic patient, at least one second clear aligner, having a second restoring force greater than the first restoring force to apply a second pressing force greater than the first pressing force to the teeth during a second period, and secondarily wearable by the orthodontic patient, and at least one third clear aligner, having a third restoring force greater than the second restoring force to apply a third pressing force greater than the second pressing force to the teeth during a third period, and tertiarily wearable by the orthodontic patient.

5 Claims, 6 Drawing Sheets

(56) References Cited

U.S. PATENT DOCUMENTS

2013/0323665 A1\* 12/2013 Dinh ...................... A61C 7/08
433/6

\* cited by examiner

CLEAR ALIGNER SET AND ORTHODONTIC TREATMENT METHOD CONSIDERING RESILIENCE OF HUMAN BODY

BACKGROUND

1. Field

The present invention relates to a clear aligner set and an orthodontic treatment method considering resilience of a human body and, more particularly, to a clear aligner set and an orthodontic treatment method considering resilience of a human body to gradually and stably treat the same orthodontic space using clear aligners formed of soft, medium, and hard materials.

2. Description of the Related Art

Orthodontic treatment may be classified into metal-brace treatment using metal braces, lingual treatment using lingual braces, and clear-aligner treatment using clear aligners.

In particular, clear-aligner treatment attracts people's attention compared to the other orthodontic treatment methods because a clear aligner covering teeth like a mouth piece is invisible, detachable, and easily wearable.

The above-described clear aligner is generally manufactured using a manual method of, for example, making a dental impression of an orthodontic patient to obtain a stone model of the teeth of the orthodontic patient, and then slightly moving every tooth of the teeth model by a skilled technician to vacuum-absorb a transparent base material onto the teeth model.

However, according to the above manual clear-aligner manufacturing method, since only one clear aligner corresponding to one orthodontic space is provided for an orthodontic patient and teeth consistently receive the same orthodontic force, the consistent application of the same orthodontic force serves as an obstacle to a recovery period in terms of resilience of a human body, for example, serves as an obstacle to the flow of blood to inhibit blood supply and thus the level of immunity is dropped to cause various infections and inflammations. In addition, the consistent application of the orthodontic force exerts a bad influence on muscles and bones and thus many problems such as ill-health occur.

SUMMARY

The present invention provides a clear aligner set and an orthodontic treatment method considering resilience of a human body to provide a sufficient adaptation period to a human body and thus constantly maintain a good level of immunity, to prevent side effects such as inflammations near teeth or weakening of the function of the teeth, to provide a sufficient recovery period in meal times or break times during orthodontic treatment and thus increase a success rate of orthodontic treatment, to reduce a retreatment rate, and to reduce pressure applied to or pain in teeth of an orthodontic patient and thus enable appropriate and easy orthodontic treatment by gradually applying a low orthodontic force, a medium orthodontic force, and then a high orthodontic force using clear aligners having the same orthodontic space but having three or more different orthodontic forces. However, the scope of the present invention is not limited thereto.

According to an aspect of the present invention, there is provided a clear aligner set considering resilience of a human body, the clear aligner set including at least one first clear aligner having a first orthodontic space therein, formed of a first transparent material, having a first restoring force to apply a first pressing force to teeth for a first wearing time a day during a first period in consideration of resilience of a human body, and primarily wearable by an orthodontic patient, at least one second clear aligner having a second orthodontic space therein, formed of a second transparent material, having a second restoring force greater than the first restoring force to apply a second pressing force greater than the first pressing force to the teeth for a second wearing time a day during a second period in consideration of the resilience of the human body, and secondarily wearable by the orthodontic patient, and at least one third clear aligner having a third orthodontic space therein, formed of a third transparent material, having a third restoring force greater than the second restoring force to apply a third pressing force greater than the second pressing force to the teeth for a third wearing time a day during a third period in consideration of the resilience of the human body, and tertiarily wearable by the orthodontic patient.

The first, second, and third clear aligners may be manufactured by high-temperature vacuum-absorbing or pressing the first, second, and third transparent materials onto one 3D-printed teeth model having desired teeth positions, respectively.

The first, second, and third orthodontic spaces may have the same shape.

To prevent unintended detachment from the teeth, each of the first, second, and third clear aligners may includes a teeth part corresponding to the teeth, a gingiva part corresponding to gingiva supporting the teeth, and a protrusion part corresponding to concave interfaces between the teeth and the gingiva.

The first, second, and third transparent materials may be resin materials based on the same polymer, the first clear aligner may have a first thickness, the second clear aligner may have a second thickness greater than the first thickness, and the third clear aligner may have a third thickness greater than the second thickness.

The first transparent material may be a soft material, the second transparent material may be a medium material, and the third transparent material may be a hard material.

The first orthodontic space may be a space corresponding to the teeth, the second orthodontic space may be a space larger than the first orthodontic space to accommodate the first clear aligner therein, and the third orthodontic space may be a space larger than the second orthodontic space to accommodate the second clear aligner therein.

According to another aspect of the present invention, there is provided an orthodontic treatment method considering resilience of a human body, the orthodontic treatment method including a first orthodontic stage for primarily wearing at least one first clear aligner having a first orthodontic space therein, formed of a first transparent material, and having a first restoring force to apply a first pressing force to teeth for a first wearing time a day during a first period in consideration of resilience of a human body, a second orthodontic stage for secondarily wearing at least one second clear aligner having a second orthodontic space therein, formed of a second transparent material, and having a second restoring force greater than the first restoring force to apply a second pressing force greater than the first pressing force to the teeth for a second wearing time a day during a second period in consideration of the resilience of the human body, and a third orthodontic stage for tertiarily wearing at least one third clear aligner having a third orthodontic space therein, formed of a third transparent material, and having a third restoring force greater than the second restoring force to apply a third pressing force greater than the second pressing force to the teeth for a third wearing time a day during a third period in consideration of the resilience of the human body.

Each of the first, second, and third periods may correspond to at least 6 days, and each of the first, second, and third wearing times may not include meal times and break times and may correspond to 15 to 21 hours a day to appropriately supply blood for recovery from inflammation.

BRIEF DESCRIPTION OF THE DRAWINGS

The above and other features and advantages of the present invention will become more apparent by describing in detail embodiments thereof with reference to the attached drawings in which.

DETAILED DESCRIPTION OF THE INVENTION

Hereinafter, the present invention will be described in detail by explaining embodiments of the invention with reference to the attached drawings.

The invention may, however, be embodied in many different forms and should not be construed as being limited to the embodiments set forth herein; rather, these embodiments are provided so that this disclosure will be thorough and complete, and will fully convey the concept of the invention to one of ordinary skill in the art. In the drawings, the thicknesses of layers are exaggerated for clarity.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of embodiments.

The terminology used herein is for the purpose of describing particular embodiments only and is not intended to be limiting of embodiments. As used herein, the singular forms "a," "an" and "the" are intended to include the plural forms as well, unless the context clearly indicates otherwise. It will be further understood that the terms "comprises" and/or "comprising" when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to schematic illustrations of idealized embodiments (and intermediate structures) of the invention. As such, variations from the shapes of the illustrations as a result, for example, of manufacturing techniques and/or tolerances, are to be expected. Thus, the embodiments of the invention should not be construed as limited to the particular shapes of regions illustrated herein, but are to include deviations in shapes that result, for example, from manufacturing.

Figure 1:
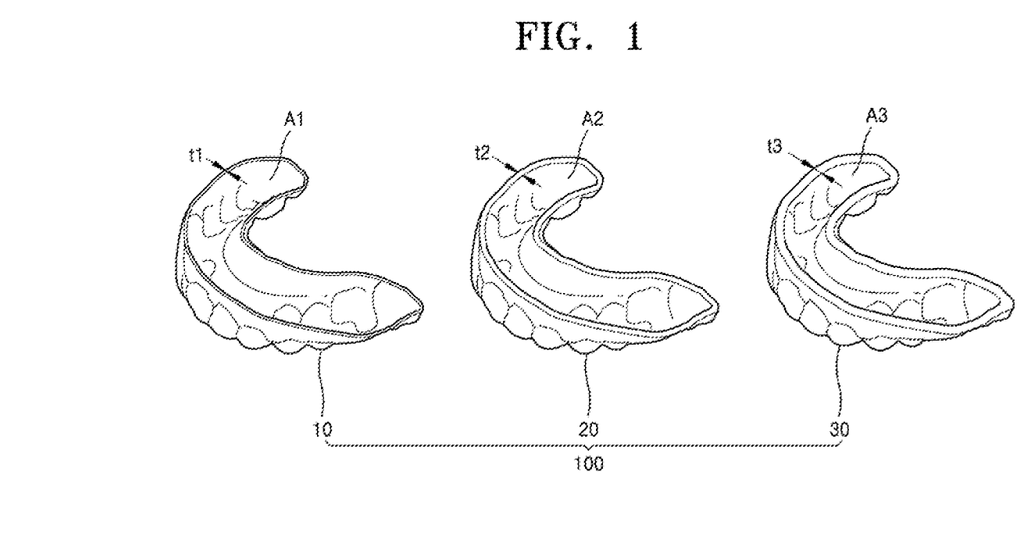
FIG. 1 is a perspective view of a clear aligner set considering resilience of a human body, according to some embodiments of the present invention.

FIG. 1 is a perspective view of a clear aligner set 100 considering resilience of a human body, according to some embodiments of the present invention.

Initially, as illustrated in FIG. 1, the clear aligner set 100 according to some embodiments of the present invention may include three or more clear aligners, e.g., a first clear aligner 10, a second clear aligner 20, and a third clear aligner 30.

Specifically, for example, as illustrated in FIG. 1, the first clear aligner 10 may be a clear aligner having a first orthodontic space A1 therein, formed of a first transparent material having a high light transmittance, having a first restoring force to apply a first pressing force to teeth T during a first period in consideration of resilience of a human body, and primarily wearable by an orthodontic patient.

Furthermore, for example, as illustrated in FIG. 1, the second clear aligner 20 may be a clear aligner having a second orthodontic space A2 therein, formed of a second transparent material, having a second restoring force greater than the first restoring force to apply a second pressing force greater than the first pressing force to the teeth T during a second period in consideration of the resilience of the human body, and secondarily wearable by the orthodontic patient.

In addition, for example, as illustrated in FIG. 1, the third clear aligner 30 may be a clear aligner having a third orthodontic space A3 therein, formed of a third transparent material, having a third restoring force greater than the second restoring force to apply a third pressing force greater than the second pressing force to the teeth T during a third period in consideration of the resilience of the human body, and tertiarily wearable by the orthodontic patient.

Figure 2:
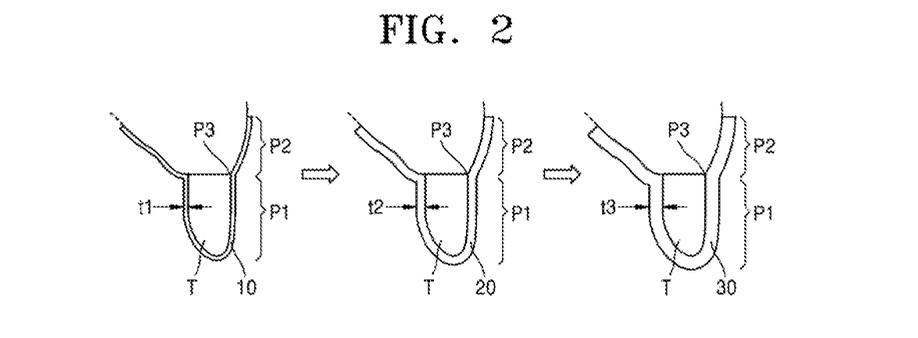
FIG. 2 is a cross-sectional view of the clear aligner set of FIG. 1.

FIG. 2 is a cross-sectional view of the clear aligner set 100 of FIG. 1.

Accordingly, as illustrated in a left part of FIG. 2, the orthodontic patient may initially wear the first clear aligner 10 having the lowest first pressing force for more than 15 hours a day during the first period, e.g., a week.

In this case, the relatively low first pressing force may be applied to the teeth T by the first clear aligner 10, and the orthodontic patient may have a sufficient preparation period necessary for orthodontic treatment. Even in this period, the orthodontic patient may remove the first clear aligner 10 from the teeth T in meal times and break times in such a manner that blood is sufficiently supplied to tissue near the teeth T, e.g., gingiva.

Subsequently, as illustrated in a middle part of FIG. 2, the orthodontic patient who has gone through the first period may wear the second clear aligner 20 having the medium second pressing force for more than 15 hours a day during the second period, e.g., another week.

In this case, the relatively medium second pressing force may be applied to the teeth T by the second clear aligner 20, and the orthodontic patient who is sufficiently adapted to the first pressing force may accept the second pressing force without excessive damage. Even in this period, the orthodontic patient may remove the second clear aligner 20 from the teeth T in meal times and break times in such a manner that blood is sufficiently supplied to tissue near the teeth T, e.g., gingiva.

Then, as illustrated in a right part of FIG. 2, the orthodontic patient who has gone through the second period may wear the third clear aligner 30 having the relatively high third pressing force for more than 15 hours a day during the third period, e.g., another week.

In this case, the relatively high third pressing force may be applied to the teeth T by the third clear aligner 30, and the orthodontic patient who is sufficiently adapted to the second pressing force may accept the third pressing force without excessive damage. Even in this period, the orthodontic patient may remove the third clear aligner 30 from the teeth T in meal times and break times in such a manner that blood is sufficiently supplied to tissue near the teeth T, e.g., gingiva.

As illustrated in FIGS. 1 and 2, to easily control the pressing forces, the first, second, and third transparent materials may be resin materials based on the same polymer, the first clear aligner 10 may have a first thickness t1 to have the first pressing force, the second clear aligner 20 may have a second thickness t2 greater than the first thickness t1 to have the second pressing force, and the third clear aligner 30 may have a third thickness t3 greater than the second thickness t2 to have the third pressing force.

For example, the first, second, and third clear aligners 10, 20, and 30 may include one or more of polyethylene oxide (also known as polyethylene glycol), polyethylene oxide-polypropylene oxide-polyethylene oxide which is a diblock or triblock copolymer including polyethylene oxide, polyethylene oxide-polybutylene oxide-polyethylene oxide polymers or a combination thereof, polypropylene, polypropylene oxide, polybutylene oxide, polytetramethylene oxide (also known as polyhydrofuran), polylactide which is an aliphatic polyester, polyglycolide, a lactide-glycolide copolymer, polybutyrate, polyvalerate, poly-ϵ-caprolactone, polyorthoester which is an aromatic polyester, polyanhydride, polydimethylsiloxane, insoluble polyvinyl, and a combination thereof, which are harmless to humans. However, the materials are not limited to those listed above.

Figure 3:
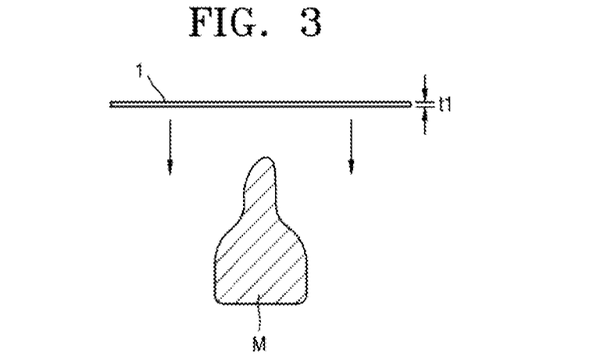
FIGS. 3 and 4 are cross-sectional views for describing a method of manufacturing a first clear aligner of the clear aligner set of FIG. 1.
Figure 4:
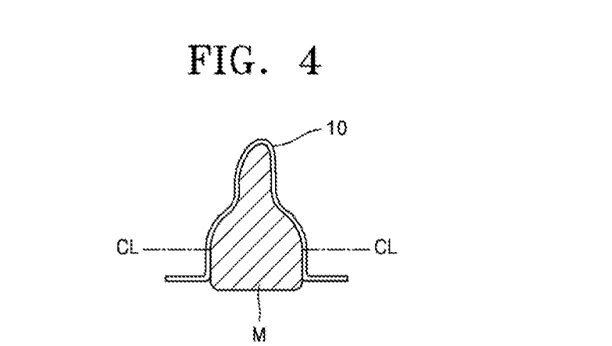

FIGS. 3 and 4 are cross-sectional views for describing a method of manufacturing the first clear aligner 10 of the clear aligner set 100 of FIG. 1.

As illustrated in FIGS. 3 and 4, the first clear aligner 10 of the clear aligner set 100 of FIG. 1 may be manufactured by high-temperature vacuum-absorbing or pressing a first base material 1 onto a 3D-printed teeth model M having desired teeth positions.

For example, the first clear aligner 10 may be manufactured by preparing the first base material 1 having the first thickness t1 above the teeth model M as illustrated in FIG. 3, high-temperature vacuum-absorbing or pressing the first base material 1 onto the teeth model M as illustrated in FIG. 4, and then cutting the same along a cutting line CL.

Figure 5:
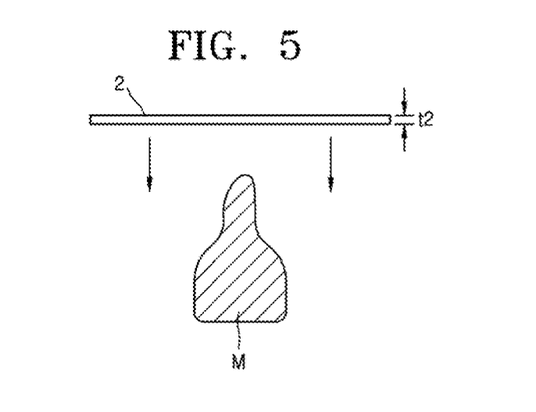
FIGS. 5 and 6 are cross-sectional views for describing a method of manufacturing a second clear aligner of the clear aligner set of FIG. 1.
Figure 6:
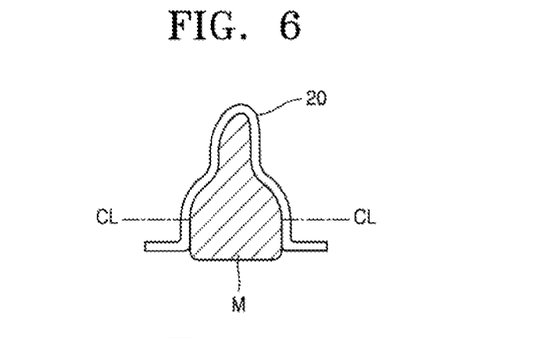

FIGS. 5 and 6 are cross-sectional views for describing a method of manufacturing the second clear aligner 20 of the clear aligner set 100 of FIG. 1.

As illustrated in FIGS. 5 and 6, the second clear aligner 20 of the clear aligner set 100 of FIG. 1 may be manufactured by high-temperature vacuum-absorbing or pressing a second base material 2 onto the above-described teeth model M.

For example, the second clear aligner 20 may be manufactured by preparing the second base material 2 having the second thickness t2 above the teeth model M as illustrated in FIG. 5, high-temperature vacuum-absorbing or pressing the second base material 2 onto the teeth model M as illustrated in FIG. 6, and then cutting the same along the cutting line CL.

Figure 7:
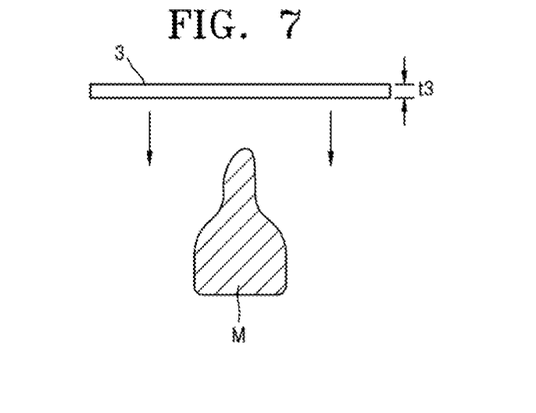
FIGS. 7 and 8 are cross-sectional views for describing a method of manufacturing a third clear aligner of the clear aligner set of FIG. 1.
Figure 8:
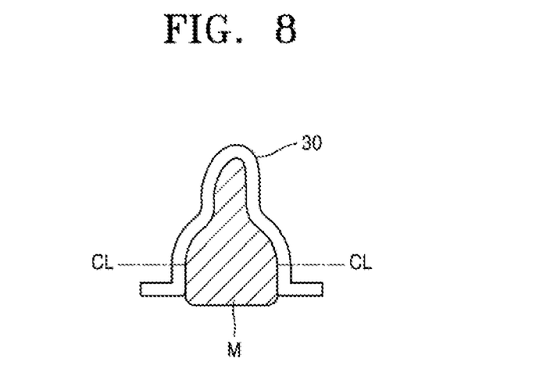

FIGS. 7 and 8 are cross-sectional views for describing a method of manufacturing the third clear aligner 30 of the clear aligner set 100 of FIG. 1;

As illustrated in FIGS. 7 and 8, the third clear aligner 30 of the clear aligner set 100 of FIG. 1 may be manufactured by high-temperature vacuum-absorbing or pressing a third base material 3 onto the above-described teeth model M.

For example, the third clear aligner 30 may be manufactured by preparing the third base material 3 having the third thickness t3 above the teeth model M as illustrated in FIG. 7, high-temperature vacuum-absorbing or pressing the third base material 3 onto the teeth model M as illustrated in FIG. 8, and then cutting the same along the cutting line CL.

Accordingly, as illustrated in FIGS. 3 to 8, since three clear aligners 10, 20, and 30 are manufactured using one teeth model M, the first orthodontic space A1 of the first clear aligner 10, the second orthodontic space A2 of the second clear aligner 20, and the third orthodontic space A3 of the third clear aligner 30 may have the same shape.

In addition, as illustrated in FIG. 2, to prevent unintended detachment from the teeth T, each of the first, second, and third clear aligners 10, 20, and 30 may include a teeth part P1 corresponding to the teeth T, a gingiva part P2 corresponding to gingiva G supporting the teeth T, and a protrusion part P3 corresponding to concave interfaces between the teeth T and the gingiva G.

Accordingly, the first, second, and third clear aligners 10, 20, and 30 of the present invention may be firmly attached and fixed to the teeth T without using a hook or a fixing device.

Although not shown in any drawing, in addition to the above-described method of manufacturing clear aligners using the same material but having different thicknesses to control an orthodontic force, i.e., a pressing force, a method of manufacturing clear aligners having the same thickness but formed of soft, medium, and hard materials may also be used.

That is, the first transparent material may be a soft material, the second transparent material may be a medium material, and the third transparent material may be a hard material.

For example, to make a polymer material soft, medium, and hard, the polymer may be mixed with different densities of a hardener or may be heated at different temperatures.

Accordingly, since a low orthodontic force, a medium orthodontic force, and then a high orthodontic force are gradually applicable using the clear aligner set 100 having the same orthodontic space A1 but having three or more different orthodontic forces, a sufficient adaptation period may be provided to a human body and thus a good level of immunity may be constantly maintained, side effects such as inflammations near teeth or weakening of the function of the teeth may be prevented, a sufficient recovery period may be provided in meal times or break times during orthodontic treatment and thus a success rate of orthodontic treatment may be increased, a retreatment rate may be reduced, and pressure applied to or pain in teeth of an orthodontic patient may be reduced and thus appropriate and easy orthodontic treatment may be enabled.

FIGS. 9 to 12 are cross-sectional views for describing a method of manufacturing a clear aligner set considering resilience of a human body, according to other embodiments of the present invention.

Figure 9:
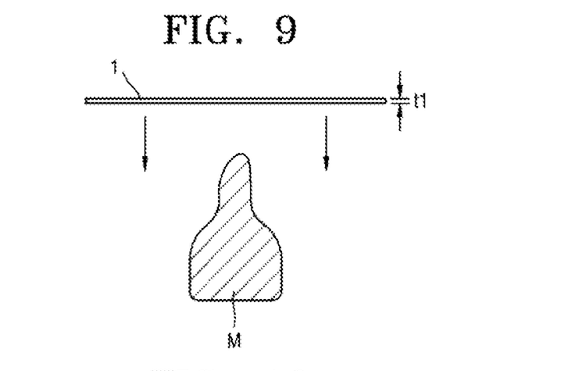
FIGS. 9 to 12 are cross-sectional views for describing a method of manufacturing a clear aligner set considering resilience of a human body, according to other embodiments of the present invention.
Figure 10:
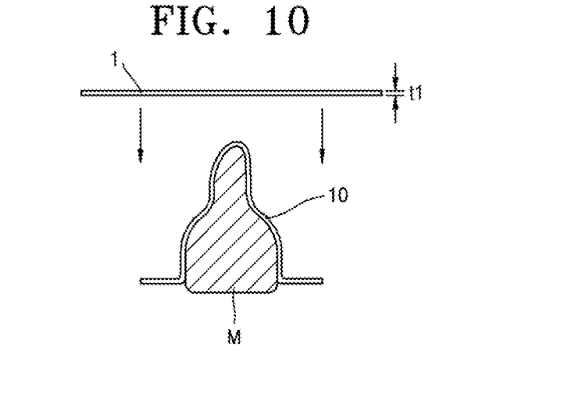

Initially, a first base material 1 having a first thickness t1 may be prepared above a teeth model M as illustrated in FIG. 9, and the first base material 1 may be vacuum-absorbed or pressed onto the teeth model M as illustrated in FIG. 10, thereby manufacturing a first clear aligner 10 of the clear aligner set according to other embodiments of the present invention. Then, a second base material 2 having the first thickness t1 may be prepared above the first clear aligner 10.

Figure 11:
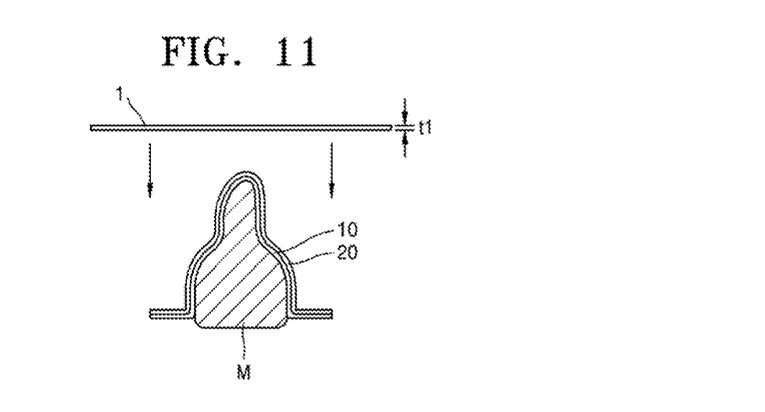

Thereafter, as illustrated in FIG. 11, the second base material 2 may be vacuum-absorbed or pressed onto the first clear aligner 10 vacuum-absorbed onto the teeth model M, thereby manufacturing a second clear aligner 20. Then, a third base material 3 having the first thickness t1 may be prepared above the teeth model M.

Figure 12:
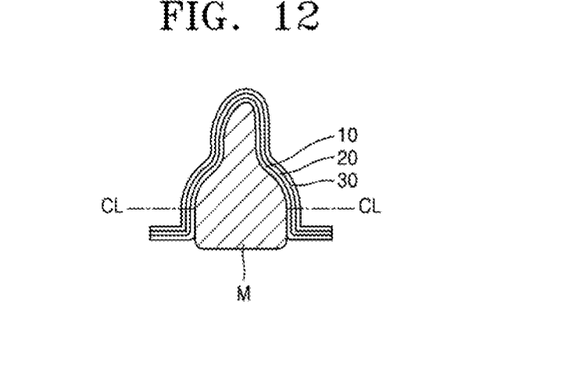

Subsequently, as illustrated in FIG. 12, the third base material 3 may be vacuum-absorbed or pressed onto the second clear aligner 20 vacuum-absorbed onto the first clear aligner 10, thereby manufacturing a third clear aligner 30. Then, the first, second, and third clear aligners 10, 20, and 30 may be cut along a cutting line CL.

Accordingly, in the clear aligner set of the present invention illustrated in FIGS. 9 to 12, a first orthodontic space A1 may be a space corresponding to teeth, a second orthodontic space A2 may be a space larger than the first orthodontic space A1 to accommodate the first clear aligner 10 therein, and a third orthodontic space A3 may be a space larger than the second orthodontic space A2 to accommodate the second clear aligner 20 therein.

Therefore, a user may simply wear the clear aligner set in such a manner that the user primarily wears the first clear aligner 10, then wears the second clear aligner 20 layered on the first clear aligner 10, and lastly wears the third clear aligner 30 layered on the second clear aligner 20. This clear aligner set is capable of reducing a storing space and a material cost thereof due to the layerable structure and the same thickness.

Figure 13:
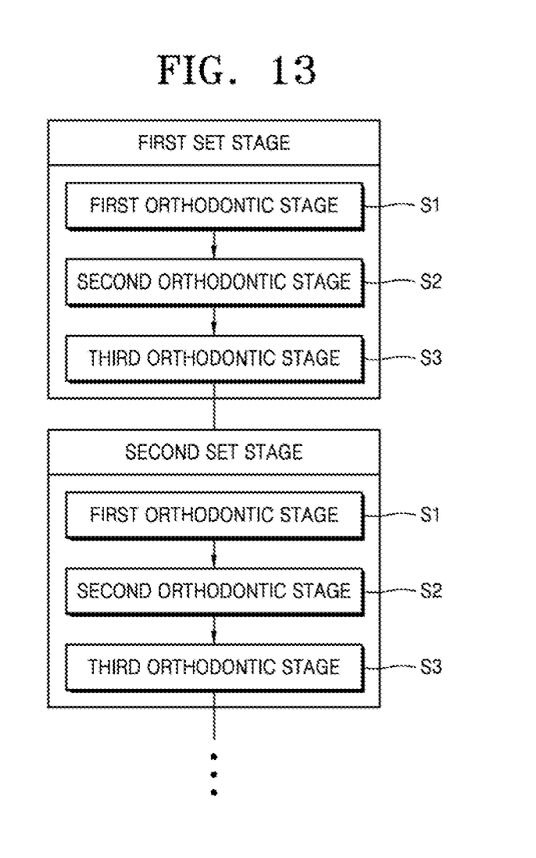
FIG. 13 is a flowchart of an orthodontic treatment method considering resilience of a human body, according to some embodiments of the present invention.

FIG. 13 is a flowchart of an orthodontic treatment method considering resilience of a human body, according to some embodiments of the present invention.

As illustrated in FIGS. 1 to 13, the orthodontic treatment method according to some embodiments of the present invention may include a first orthodontic stage S1 for primarily wearing at least one first clear aligner 10 having a first orthodontic space A1 therein, formed of a first transparent material, and having a first restoring force to apply a first pressing force to teeth T for a first wearing time a day during a first period in consideration of resilience of a human body, a second orthodontic stage S2 for secondarily wearing at least one second clear aligner 20 having a second orthodontic space A2 therein, formed of a second transparent material, and having a second restoring force greater than the first restoring force to apply a second pressing force greater than the first pressing force to the teeth T for a second wearing time a day during a second period in consideration of the resilience of the human body, and a third orthodontic stage S3 for tertiarily wearing at least one third clear aligner 30 having a third orthodontic space A3 therein, formed of a third transparent material, and having a third restoring force greater than the second restoring force to apply a third pressing force greater than the second pressing force to the teeth T for a third wearing time a day during a third period in consideration of the resilience of the human body.

In this case, each of the first, second, and third periods may correspond to at least 6 days, and each of the first, second, and third wearing times may not include meal times and break times and may correspond to 15 to 21 hours a day to appropriately supply blood for recovery from inflammation.

Furthermore, as illustrated in FIG. 13, the teeth T may be gradually straightened without excessive damage by repeating the above-described procedure using, for example, three clear aligners.

Therefore, since gradually increasing orthodontic forces are applicable, a sufficient adaptation period may be provided to a human body and thus a good level of immunity may be constantly maintained, side effects such as inflammations near teeth or weakening of the function of the teeth may be prevented, a sufficient recovery period may be provided in meal times or break times during orthodontic treatment and thus a success rate of orthodontic treatment may be increased, a retreatment rate may be reduced, and pressure applied to or pain in teeth of an orthodontic patient may be reduced and thus appropriate and easy orthodontic treatment may be enabled.

As described above, according to some embodiments of the present invention, since gradually increasing orthodontic forces are applicable, a sufficient adaptation period may be provided to a human body and thus a good level of immunity may be constantly maintained, side effects such as inflammations near teeth or weakening of the function of the teeth may be prevented, a sufficient recovery period may be provided in meal times or break times during orthodontic treatment and thus a success rate of orthodontic treatment may be increased, a retreatment rate may be reduced, and pressure applied to or pain in teeth of an orthodontic patient may be reduced and thus appropriate and easy orthodontic treatment may be enabled. However, the scope of the present invention is not limited to the above effects.

While the present invention has been particularly shown and described with reference to embodiments thereof, it will be understood by those of ordinary skill in the art that various changes in form and details may be made therein without departing from the spirit and scope of the present invention as defined by the following claims.

What is claimed is:

1. A clear aligner set considering resilience of a human body, the clear aligner set comprising:
at least one first clear aligner having a first orthodontic space therein, formed of a first transparent material, having a first restoring force to apply a first pressing force to teeth for a first wearing time a day during a first period in consideration of the resilience of a human body, and primarily wearable by an orthodontic patient;
at least one second clear aligner having a second orthodontic space therein, formed of a second transparent material, having a second restoring force greater than the first restoring force to apply a second pressing force greater than the first pressing force to the teeth for a second wearing time a day during a second period in consideration of the resilience of the human body, and secondarily wearable by the orthodontic patient;
at least one third clear aligner having a third orthodontic space therein, formed of a third transparent material, having a third restoring force greater than the second restoring force to apply a third pressing force greater than the second pressing force to the teeth for a third wearing time a day during a third period in consideration of the resilience of the human body, and tertiarily wearable by the orthodontic patient;

wherein the first orthodontic space is a space corresponding to the teeth;

wherein the second orthodontic space is a space larger than the first orthodontic space to accommodate the at least one first clear aligner therein; and wherein the third orthodontic space is a space larger than the second orthodontic space to accommodate the at least one second clear aligner therein.

2. The clear aligner set of claim 1, wherein the at least one first clear aligner is manufactured by high-temperature vacuum-absorbing or pressing the first transparent material onto one 3D-printed teeth model having desired teeth positions, wherein the at least one second clear aligner is manufactured by high-temperature vacuum-absorbing or pressing the second transparent material onto the at least one first clear aligner, wherein the at least one third clear aligner is manufactured by high-temperature vacuum-absorbing or pressing the third transparent material onto the at least one second clear aligner.

3. The clear aligner set of claim 1, wherein, to prevent unintended detachment from the teeth, the at least one first clear aligner comprises:

a teeth part corresponding to the teeth;

a gingiva part corresponding to gingiva supporting the teeth; and a protrusion part corresponding to concave interfaces between the teeth and the gingiva.

4. The clear aligner set of claim 1, wherein the first, second, and third transparent materials are resin materials based on the same polymer, wherein the at least one first, second and third clear aligners have the same thickness.

5. The clear aligner set of claim 1, wherein the first transparent material is a soft material, wherein the second transparent material is a medium material, and wherein the third transparent material is a hard material.

* * * * *